United States Patent
Lorenz

(10) Patent No.: US 7,764,813 B2
(45) Date of Patent: Jul. 27, 2010

(54) REGION DELINEATION IN COMPUTER TOMOGRAPHIC ANGIOGRAPHY

(75) Inventor: Cristian Lorenz, Hamburg (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 1013 days.

(21) Appl. No.: 10/554,355

(22) PCT Filed: Apr. 14, 2004

(86) PCT No.: PCT/IB2004/050435

§ 371 (c)(1),
(2), (4) Date: Aug. 8, 2006

(87) PCT Pub. No.: WO2004/095371

PCT Pub. Date: Nov. 4, 2004

(65) Prior Publication Data

US 2007/0058849 A1    Mar. 15, 2007

(30) Foreign Application Priority Data

Apr. 24, 2003  (EP) .................... 03101124

(51) Int. Cl.
*G06K 9/00* (2006.01)
*G06K 9/46* (2006.01)
*G06K 9/66* (2006.01)
*G06K 9/62* (2006.01)

(52) U.S. Cl. .................. 382/128; 382/131; 382/132; 382/199; 382/203; 382/209

(58) Field of Classification Search ................ 382/128, 382/132, 190, 195, 199, 203, 204, 205, 209, 382/224, 280

See application file for complete search history.

(56) References Cited

U.S. PATENT DOCUMENTS 5,570,404 A  *  10/1996  Liang et al. ............... 378/8

(Continued)

FOREIGN PATENT DOCUMENTS

EP          1 030 187 A2      8/2000

(Continued)

OTHER PUBLICATIONS

Philip et al. (Automatic Detection of Myocardial Contours in Cine-Computed Tomographic Images, IEEE Transactions on Medical Imaging, vol. 13, No. 2, Jun. 1994, pp. 241-253).*

(Continued)

*Primary Examiner*—Tom Y Lu
*Assistant Examiner*—Thomas A Conway

(57) ABSTRACT

The semi-automatic extraction and delineation of the cardiac region of interest in computer tomographic angiography images is time consuming and requires an experienced operator. According to the present invention, a completely automatic delineation and extraction of the CROI is provided, wherein the chest wall is detected and the region where the CROI is attached to the chest wall. Then, the descending aorta is detected. After that a circular initialization of a closed contour around a part of the CROI is performed, which is optimized in a subsequent step. Then, a propagation is performed through all slices of the CTA image, where the preceding contour of the preceding slice image is used for an actual contour optimization in the actual slice image. Advantageously, a fully automatic delineation and extraction of the CROI is provided within very short time.

19 Claims, 3 Drawing Sheets

U.S. PATENT DOCUMENTS

| | | | |
|---|---|---|---|
| 5,832,134 | A | 11/1998 | Avinash et al. |
| 6,249,594 | B1 * | 6/2001 | Hibbard .................. 382/128 |
| 6,335,980 | B1 | 1/2002 | Armato et al. |
| 7,206,462 | B1 * | 4/2007 | Betke et al. ............... 382/280 |
| 2001/0056230 | A1 * | 12/2001 | Barak et al. ............... 600/407 |
| 2002/0191827 | A1 | 12/2002 | Armato et al. |

FOREIGN PATENT DOCUMENTS

| | | |
|---|---|---|
| EP | 1 225 541 A2 | 7/2002 |

OTHER PUBLICATIONS

Stetten (Active Fourier Contour Applied to Real Time 3D Ultrasound of the Heart, International Journal of Image and Graphics, vol. 1, No. 4, 2001, pp. 647-658).*

Wever et al. (Maximal aneurysm Diameter Follow-up is Inadequate after Endovascular Abdominal Aortic Aneurysm Repair, European Journal of Vascular and Endovascular Surgery, Harcourt Publishers, 2000, vol. 20, Issue 2, pp. 177-182).*

Bister, M., et al.; Automated Segmentation of Cardiac MR Images; 1991; Proc. Comp. in Cardiology Mtg.; 17:697-700.

Ezrielev, J., et al.; An Image Editor for a 3D-CT Reconstruction System; 1990; SPIE; 1233:67-76.

Hammoude, A.; A Contour Extraction Algorithm for Echocardiographic Images; 1997; Computers in Cardiology; 24:537-540.

Kuhl, F.P., et al.; Elliptic Fourier Features of a Closed Contour; 1982; Computer Graphics and Image Proc.; 18:236-258.

Yu, Y., et al.; Image Segmentation Based on Region Growing and Edge Detection; 1999; IEEE-SMC Conf. Proc.; pp. 798-803.

* cited by examiner

REGION DELINEATION IN COMPUTER TOMOGRAPHIC ANGIOGRAPHY

The present invention relates to the field of medical digital imaging. In particular, the present invention relates to a method for the automatic delineation or extraction of a first region, which is the cardiac region of interest (CRO), adjacent to a chest wall in computer tomography angiography images, to an image processing device, to a computer tomographic system and to a computer program for an image processing device.

CT (computer tomography) angiography (CTA) is an examination that uses x-rays to visualize blood flow in arterial vessels throughout the body. From arteries serving the brain, to cells bringing blood to the lungs, kidneys and the arms and legs. CT combines the use of x-rays with computerized analysis of the images. Beams of x-rays are passed from a rotating gantry through the area of interest in a patient's body from several different angles, so as to generate cross-sectional slice images, which are assembled into a two or three-dimensional pictures of the area being studied.

Compared to catheter angiography, which involves injecting contrast material into an artery, CTA is much less invasive and a more patient-friendly procedure. Contrast material is injected into a vein rather than an artery. Preferably for acquiring CTA images, CT scanners of an advanced type called spiral CT scanners are used.

CTA imaging is often performed in the cardiac region of interest.

Numerous interactive schemes and methods have been proposed in the prior art to help users edit images more efficiently. One example of such a method is described in an article entitled "An Image Editor for a 3D-CT Reconstruction System" by Jay Ezrielev et al, published in Proceedings of Medical Imaging IV, Image Processing, Newport Beach, vol. 1233. The authors of this article discuss an image editing system which utilizes intelligent and semi-automatic methods to improve the speed and efficiency of the editing process. Some functions are provided in the editing system, which operate on entire image sets instead of individual images. These functions are capable of accomplishing thresholding operations or operations that remove simple objects from the dataset. Manuel editing functions are also provided to accomplish operations that the semi-automatic methods are not capable of performing.

U.S. Pat. No. 5,570,404 describes a method for automatically editing a plurality of CT image slices to provide a three-dimensional view of a selected object located within a patient's body, which comprises the provision of at least one slab of CT image slices, generated by CT scanning systems and computing a top MIP image of the slab. An undesirable object is removed from the top MIP image by firstly detecting all the pixels having illuminating intensity values, which represent the undesirable object. Secondly, all the pixels of the region to be removed are set to a substantially zero illuminating intensity value, in order to remove the object from the top MIP image of the slab. After the undesirable object is removed from the top MIP image, the edits made thereto are applied to each CT image slice in the slab. This document also describes an apparatus for performing a 3D reconstruction of CT angiographic images to visualize a selected object located within a patient's body.

However, the known methods and apparatus usually require an interaction by a user to identify desired or undesired parts of an image. Furthermore, the processing speed, i.e. the time required to process the image for display to a user is always a critical concern. In particular, in the case of imaging the cardiac region of interest.

It is an object of the present invention to provide for an improved imaging of the cardiac region of interest.

According to an exemplary embodiment of the present invention, the above object may be solved with a method for the automatic delineation or extraction of the cardiac region of interest adjacent to a chest wall in computer tomography angiography images is set forth in claim 1. The method comprises the steps of determining the wall of the chest, determining another region where the cardiac region of interest is attached to the chest wall, determining an aorta in the cardiac region of interest. Then, a closed contour is initialized around the cardiac region of interest. In a following step, a shape of this closed contour is optimized.

According to this exemplary embodiment of the present invention, a fully automatic delineation and extraction of the cardiac region of interest in computer tomography angiography images may be provided. Advantageously, this allows for a generation of images including only the cardiac region of interest without the interaction of an operator. In clinical applications, the method according to the present invention may allow for improved diagnostics, since objects which are not part of the cardiac region of interest are not displayed to a user. Furthermore, the above method is highly time efficient. Tests showed that the above method allows for the complete automatic delineation of the cardiac region of interest in approximately 5 seconds on a standard PC, including, for example, an Intium Pentium IV Processor.

According to another exemplary embodiment of the present invention as set forth in claim 2, the optimization of the shape of the closed contour is performed by using a Fourier interpolation and an edge criterion. Advantageously, this allows for a very fast and precise optimization of the closed contour.

According to another exemplary embodiment of the present invention as set forth in claim 3, the wall of the chest is determined by using a threshold criterion and by casting search rays from a front of the chest to a back of the chest. Advantageously, this may allow for a very simple and efficient segmentation of the chest wall.

According to another exemplary embodiment of the present invention as set forth in claim 4, the descending aorta is determined by use of a threshold diameter criterion and by casting search rays from a left side of the chest to a right side of the chest, which allows for a complete automatic segmentation of the aorta while requiring only a minimal number of process steps to be carried out According to another exemplary embodiment of the present invention as set forth in claim 5, the optimized shape contour of the preceding slice image is inherited from the preceding slice image for the closed contour initialization. Advantageously, this increases the time efficiency of the method and the preciseness of the method since the closed contour from which the optimization of the shape is started in each image becomes more precise from image slice to image slice.

According to another exemplary embodiment of the present invention as set forth in claim 6, an image processing device for the automatic delineation or extraction of the cardiac region of interest adjacent to a chest wall in computer tomographic angiography images is provided, which advantageously allows for the completely automatic delineation and extraction of the cardiac region of interest within a very short time. Also, due to the fact that only a reduced number of steps is carried out in the image processing device according to the present invention, an image processing device can be provided requiring a less powerful processor and less storage capacity than other systems known in the art.

According to another exemplary embodiment of the present invention as set forth in claim 7, an image processing device is provided allowing for a precise delineation and extraction of the cardiac region of interest.

According to another exemplary embodiment of the present invention, a computer tomographic system as set forth in claim 8 is provided, allowing for a completely automatic delineation or extraction of the cardiac region of interest. Claim 9 provides for another exemplary embodiment of the tomographic system.

The present invention relates also to a computer program for an image processing device for the automatic delineation or extraction of the cardiac region of interest. The computer program according to the present invention is defined in claim 10. The computer program according to the present invention is preferably loaded into a working memory of an image processor. The image processor is thus equipped to carry out the method of the invention. The computer program may be stored on a computer readable medium, such as a CD-Rom. The computer program may also be presented over a network such as the WorldWideWeb and can be downloaded into the working memory of the image processor from such a network.

It may be seen as the gist of an exemplary embodiment of the present invention that a completely automatic delineation and extraction of the cardiac region of interest in computer tomographic angiography images is provided. Firstly, the chest wall is detected by using a threshold criterion by casting search rays from front to back. Then, a detection of the region where the cardiac region of interest is attached to the chest wall (close to the sternum) is carried out. Then, a detection of the descending aorta using a threshold and diameter criterion by casting search rays from left to right is performed. After that, a circular initialization of a closed contour around the cardiac region of interest between aorta and sternum is performed in a suitable slice image. Then, an optimization of the contour shape by using a Fourier interpolation and edge criterion is performed. A propagation through all slices is performed where a preceding contour of a preceding slice is inherited in an active slice image, which is then shape optimized in the active slice. As a result, a representation of an image part (region of interest) is generated, which contains the cardiac structures, i.e. left and right ventricles, left and right atriums, first part of the ascending aorta, coronary arteries and the trunk of connections between atria and ventricles and the pulmonary vasculature.

These and other aspects of the present invention are apparent from and will be elucidated with reference to the embodiments described hereinafter and with reference to the following drawings.

Figure 1:
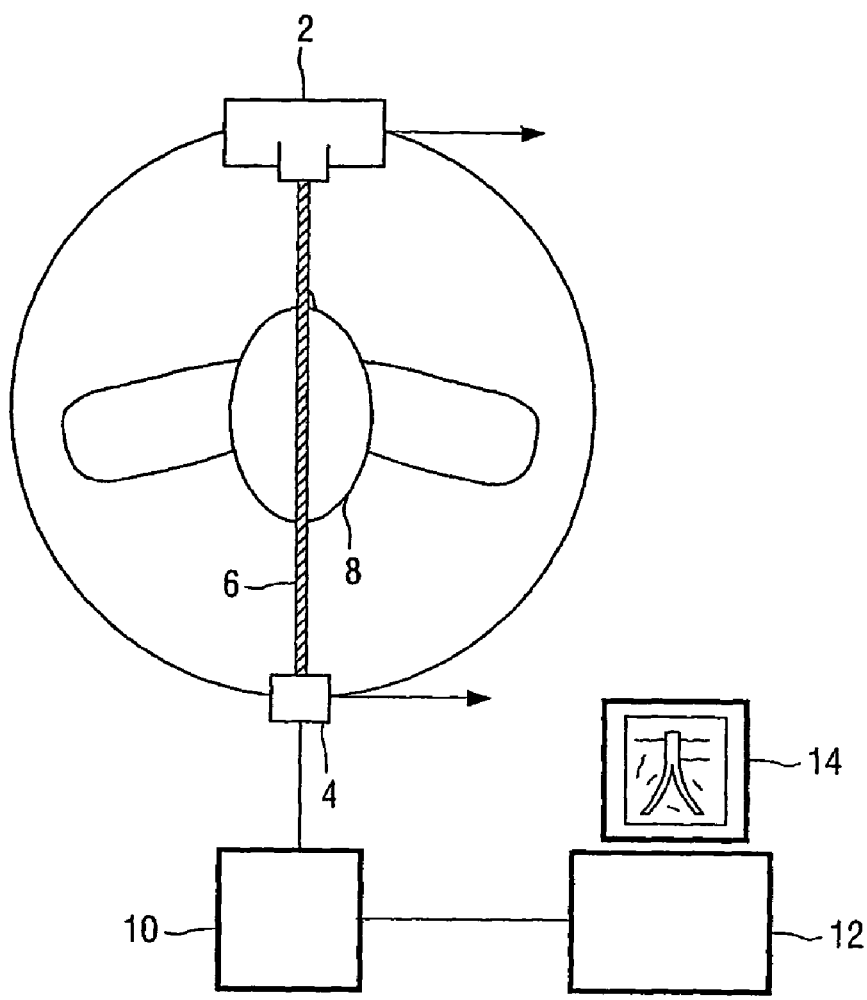
FIG. 1 shows an exemplary embodiment of a CT system according to the present invention.

FIG. 1 shows a simplified representation of an exemplary embodiment of a CT system according to the present invention. Reference numeral 2 in FIG. 1 designates an x-ray tube and reference numeral 4 designates a radiation detector. As is well known in the art, in order to generate an image of a body slice of interest, the x-ray tube 2 projects a thin x-ray beam 6 through the object slice of the subject 8 under study. The attenuation of the x-ray beam 6 is determined for a large number of paths through the object slice. The radiation intensity is recorded by the detector 4 for each path through the object slice. The detector 4 is coupled to a measurement electronics device 10 for further processing the measurement values sensed by the detector 4. The measurement electronics device 10 is coupled to an image processing device 12, such as a computer, including, for example a Pentium IV processor. The image processing device 12 processes coded measurement values and calculates a two or three-dimensional attenuation distribution. The attenuation distribution generally comprises a numerical matrix, which is stored in a memory of the image processing device 12.

The image processing device 12 is coupled to a display 14, which converts the numerical matrix into an image which can be viewed by the operator. Each point or pixel of the image corresponds to a matrix element. As is well known in the art, the illuminating intensity value of each pixel represents the amount of attenuation caused by the object scanned in the object slice.

As is well known in the art, the numerical matrix comprises a plurality of slice images, each corresponding to a scan path. For forming the matrix, the slice images are stacked.

Figure 2:
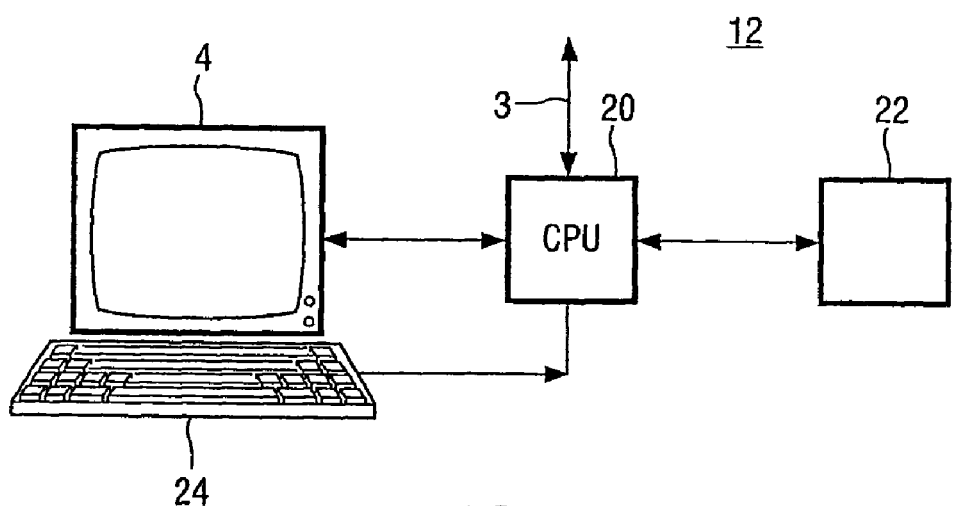
FIG. 2 shows an exemplary embodiment of an image processing device according to the present invention, as it may be used in the CT system of FIG. 1.

FIG. 2 shows an exemplary embodiment of the image processing device 12 according to the present invention. For executing an exemplary embodiment of a method in accordance with the present invention. The image processing device 12 depicted in FIG. 2 comprises a central processing unit (CPU) or image processor 20, which, as already mentioned above, may for example be a Pentium IV processor. The image processor 20 is connected to a memory 22 for storing the coded measurement values and the numerical matrix and the generated images. The image processor 20 may be connected to a plurality of input/output network or diagnosis devices. In the present case, as depicted in FIG. 1, the image processor 20 is connected to a CT scanner. The image processor 20 is furthermore connected to the display device 14 (for example a computer monitor) for displaying information or images computed or adapted in the image processor 20. An operator may interact with the image processor 20 via a keyboard 24 and/or other output devices, which are not depicted in FIG. 2.

Figure 3:
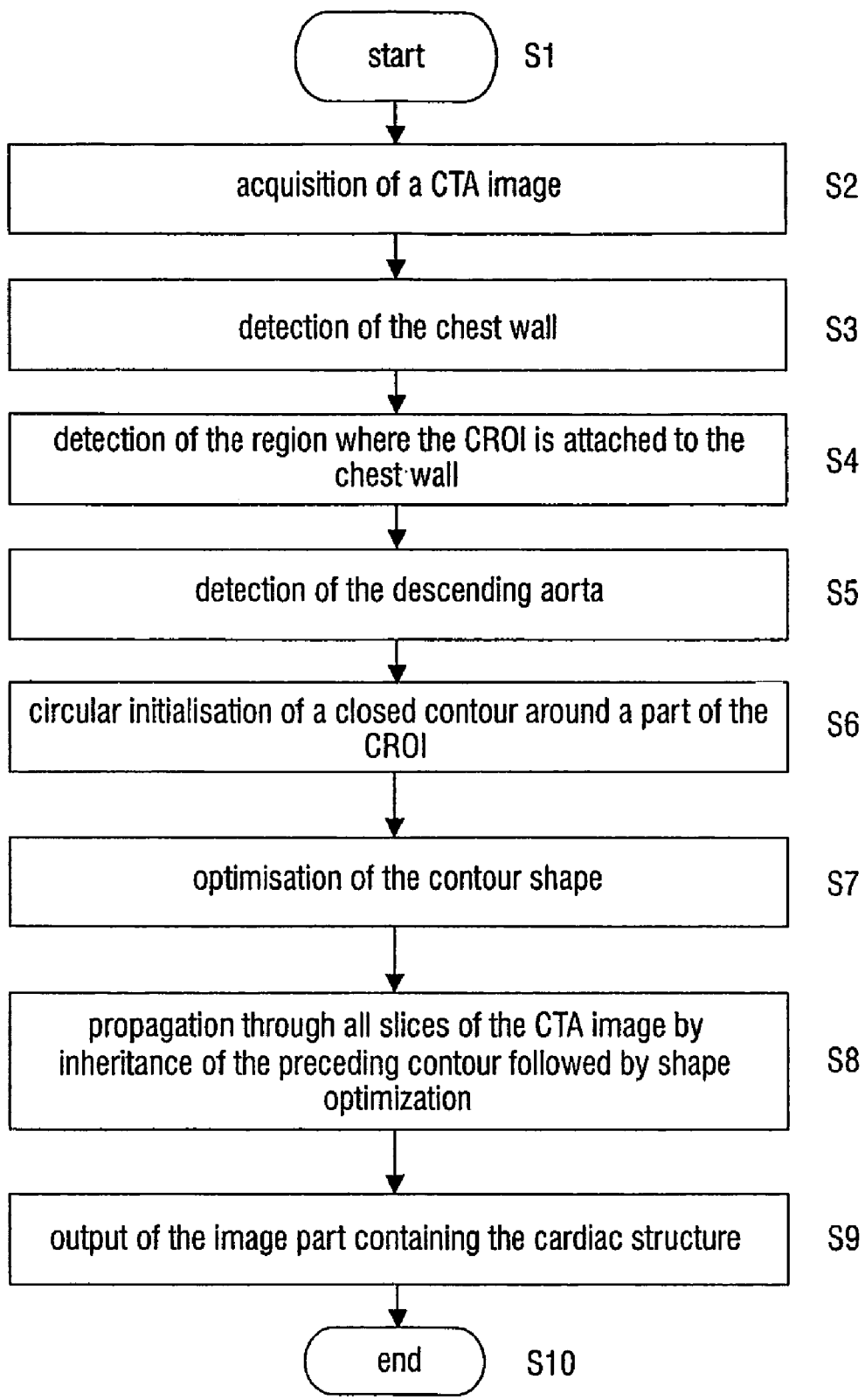
FIG. 3 shows a flow-chart of an exemplary embodiment of a method for operating the CT system of FIG. 1, including the image processing device of FIG. 2.

FIG. 3 shows a flow-chart of an exemplary embodiment of a method of operating the image processing device according to the present invention. After the start in step S1, the method continues to step S2, where a CTA image consisting of a plurality of CTA image slices is acquired by means of the CT scanner. Then, the method continues to step S3, where a detection of the chest wall is carried out According to an aspect of the present invention, the detection of the chest wall is carried out by using a threshold criterion by casting search rays from the front of the chest to the back of the chest. Then, the method continues to step S4, where a determination of a region is performed, where the cardiac region of interest (CROI) is attached to the chest wall. This region is close to the sternum. This is performed in all slices, or in a sub-set of slices, e.g. every third slice, (i.e. in every n'th slice). Then, the method continues to step S5, where a detection of the descending aorta is carried out by using a threshold and diameter criterion by casting search rays from a left side of the chest to a right side of the chest. As for step S4, the step S5 is carried out in all slices, or in a sub-set of slices, leading to a set of candidates for the aorta center. The candidates are clustered using a distance criterion, i.e. candidates close to each other are collected in the same cluster. Subsequently, the cluster containing the most candidates is accepted as aorta-cluster. Then, in a subsequent step S6, a circular initialization of a closed contour around the CROI between the aorta and sternum is carried out in a suitable slice image, namely in a slice with a small contact region between chest-wall and cardiac tissue. In a subsequent step S7, the contour initialized in step S6 is optimized by using Fourier interpolation and an edge criterion. Then, the method continues to step S8.

In step S8, the above step S7 is carried out, i.e. are propagated through all slice images or a sub-set of slices of the CTA image acquired in step S2. During the propagation, in each actual slice image, a contour of the preceding propagation is inherited, i.e. is used as the initialization contour instead of a circular contour in step S6.

Then, after step S8, the method continues to step S9, where a representation of the image part (region of interest), which contains the cardiac structures, i.e. left and right ventricles, left and right atrium, first part of the ascending aorta, coronary arteries and the trunk of connections between atria and ventricles and the pulmonary vasculature is output to a user via display 14. Then, the method continues to step S10, where it ends.

The method described with reference to FIG. 3 has an improved efficiency in comparison to known systems. The described method allows the completely automatic delineation of the CROI in approximately 5 seconds on a standard PC. Furthermore, this method does not require user assistance. Furthermore, advantageously, the above method allows for an immediate visualization. The method allows for immediate visualization of the cardiac structures after image loading on the medical image processing device. In current systems, after image loading, the cardiac region of interest needs to be interactively delineated in order to eliminate disturbing substances, such as for example the rib-cage from visualization, which is not necessary in the method according to the present invention, since this is automatically carried out by the method. Furthermore, the above method allows focusing post-processing (for example the suppression of contrast filled heart chambers for visualization or the extraction of the coronary arteries) automatically to the cardiac region of interest, leading to a reduction of processing time. Furthermore, an effect provided by the above method supplies a set of anatomic reference points (for example the descending aorta and the chest wall, which can be used for further processing, such as the automatic extraction of the coronary arteries).

Figure 4A:
FIGS. 4a to 4c show examples of CTA images.
Figure 4B:
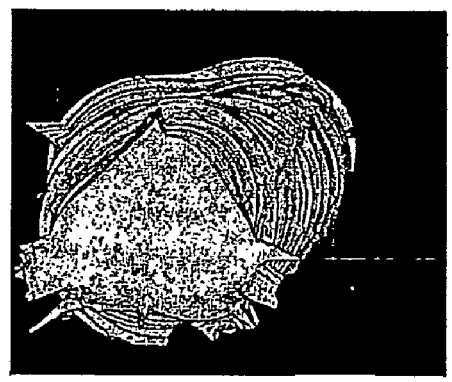
Figure 4C:
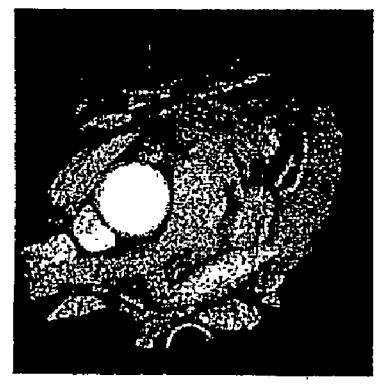

FIGS. 4a to 4c show images generated in accordance with the method described with reference to FIG. 3. FIG. 4a shows a CT slice with a cardiac ROI (region of interest), where the descending aorta is marked with a cross. FIG. 4b shows a surface rendering of the cardiac ROI. As may be taken from FIG. 4b, only the cardiac ROI is displayed and no other disturbing structures are in the image.

FIG. 4c shows a volume rendering of the CROI also generated in accordance with the method described with reference to FIG. 3 in accordance with an exemplary embodiment of the present invention. As may be taken from FIG. 4c, only the image part is displayed which contains the cardiac structures, i.e. left and right ventricles, left and right atrium, first part of the ascending aorta, coronary arteries and the trunk of connections between atria and ventricles and the pulmonary vasculature. No other elements which may disturb the visualization of the CROI are displayed in this image.

The invention claimed is:

1. A method comprising:
identifying with a processor a first region in an image, wherein the first region is a cardiac region of interest (CROI) adjacent to a chest wall;
determining with the processor the chest wall in the image;
identifying with the processor a sternum of the chest wall in the image;
determining with the processor a second region where the first region is attached to the chest wall close to the sternum;
wherein the second region is not an epicardium;
determining with the processor an aorta in the first region;
initializing with the processor a closed contour around a sub-region of the first region between the aorta and the sternum; and
optimizing with the processor a shape of the closed contour.

2. The method of claim 1, wherein the step of optimizing the shape of the closed contour is performed by using a Fourier interpolation and an edge criterion.

3. The method of claim 1, wherein the chest wall is determined by using a threshold criterion and by casting search rays from a front of a chest to a back of the chest.

4. The method of claim 1, wherein the aorta, which is descending, is determined by using a threshold diameter criterion and by casting search rays from a left side of a chest to a right side of the chest.

5. The method of claim 1, wherein the image consists of a plurality of slice images; wherein the steps of claim 1 are repeated for the slice images; and wherein for each slice image, the optimized shape contour of the preceding slice image is inherited for the closed contour initialization.

6. An image processing device comprising an image processor which performs the following operation:
identifying a first region in an image, wherein the first region is a cardiac region of interest (CROI) adjacent to a chest wall;
determining the chest wall in the image;
identifying a sternum of the chest wall in the image;
determining a second region where the first region is attached to the chest wall close to the sternum;
wherein the second region is not an epicardium;
determining an aorta in the first region;
initializing a closed contour around a sub-region of the first region between the aorta and the sternum;
and optimizing a shape of the closed contour.

7. The image processing device of claim 6, wherein the step of optimizing the shape of the closed contour is performed by using a Fourier interpolation and an edge criterion;
wherein the chest wall is determined by using a threshold criterion and by casting search rays from a front of a chest to a back of the chest; wherein the aorta, which is descending, is determined by using a threshold diameter criterion and by casting search rays from a left side of the chest to a right side of the chest;
wherein the image consists of a plurality of slice images; wherein the operation-steps of claim 6 are repeated for the slice images; and
wherein for each slice image, the optimized shape contour of the preceding slice image is inherited for the closed contour initialization.

8. The image processing device of claim 6, wherein initializing the closed contour around the sub-region of the first region between the aorta and sternum is carried out in a slice with a small contact region between the chest wall and cardiac tissue, wherein at least two slices have different sized contact regions.

9. A computer tomographic (CT) system including an image processor which performs the following operations:

identifying a first region in an image, wherein the first region is a cardiac region of interest (CROI) adjacent to a chest wall;
determining the chest wall in the image;
identifying a sternum of the chest wall in the image;
determining a second region where the first region is attached to the chest wall close to the sternum;
wherein the second region is not an epicardium;
determining an aorta in the first region;
initializing a closed contour around a sub-region of the first region between the aorta and the sternum; and
optimizing a shape of the closed contour.

10. The computer tomographic (CT) system of claim 9, wherein the step of optimizing the shape of the closed contour is performed by using a Fourier interpolation and an edge criterion;
wherein the chest wall is determined by using a threshold criterion and by casting search rays from a front of a chest to a back of the chest;
wherein the aorta, which is descending, is determined by using a threshold diameter criterion and by casting search rays from a left side of the chest to a right side of the chest;
wherein the image consists of a plurality of slice images;
wherein the operation-steps of claim 8 are repeated for the slice images; and
wherein for each slice image, the optimized shape contour of the preceding slice image is inherited for the closed contour initialization.

11. The computer tomographic (CT) system of claim 9, wherein the operation of optimizing the shape of the closed contour is performed by using a Fourier interpolation and an edge criterion.

12. The computer tomographic (CT) system of claim 9, wherein the chest wall is determined by using a threshold criterion and by casting search rays from a front of a chest to a back of the chest.

13. The computer tomographic (CT) system of claim 9, wherein the aorta, which is descending, is determined by using a threshold diameter criterion and by casting search rays from a left side of a chest to a right side of the chest.

14. The computer tomographic (CT) system of claim 9, wherein the image consists of a plurality of slice images; wherein the steps of claim 1 are repeated for the slice images; and wherein for each slice image, the optimized shape contour of the preceding slice image is inherited for the closed contour initialization.

15. A non-transitory computer readable storage medium containing computer executable instructions for an image processing device, wherein the computer executable instructions cause the image processing device to perform the following operations when executed on the image processing device:
identifying a first region in an image, wherein the first region is a cardiac region of interest (CROI) adjacent to a chest wall;
determining the chest wall in the image;
identifying a sternum of the chest wall in the image;
determining a second region where the first region is attached to the chest wall close to the sternum;
wherein the second region is not an epicardium;
determining an aorta in the first region;
initializing a closed contour around a sub-region of the first region between the aorta and sternum; and
optimizing a shape of the closed contour.

16. The computer readable medium of claim 15, wherein the operation of optimizing the shape of the closed contour is performed by using a Fourier interpolation and an edge criterion.

17. The computer readable medium of claim 15, wherein the chest wall is determined by using a threshold criterion and by casting search rays from a front of a chest to a back of the chest.

18. The computer readable medium of claim 15, wherein the aorta, which is descending, is determined by using a threshold diameter criterion and by casting search rays from a left side of a chest to a right side of the chest.

19. The computer readable medium of claim 15, wherein the image consists of a plurality of slice images; wherein the steps of claim 10 are repeated for the slice images; and wherein for each slice image, the optimized shape contour of the preceding slice image is inherited for the closed contour initialization.

* * * * *